US008137679B2

(12) United States Patent
Nash et al.

(10) Patent No.: US 8,137,679 B2
(45) Date of Patent: Mar. 20, 2012

(54) **IMMUNOGEN ADHERENCE INHIBITOR DIRECTED TO *LACTOBACILLUS* ORGANISMS AND METHOD OF MAKING AND USING IT**

(75) Inventors: Peter Nash, Eden Prairie, MN (US); Bradley M. Mitteness, Ghent, MN (US)

(73) Assignee: Camas Incorporated, Le Center, MN (US)

( * ) Notice: Subject to any disclaimer, the term of this patent is extended or adjusted under 35 U.S.C. 154(b) by 216 days.

(21) Appl. No.: 12/352,333

(22) Filed: Jan. 12, 2009

(65) Prior Publication Data

US 2009/0117129 A1    May 7, 2009

Related U.S. Application Data

(63) Continuation of application No. 11/784,868, filed on Apr. 10, 2007, now abandoned.

(51) Int. Cl.
*A61K 39/02* (2006.01)
*A61K 49/00* (2006.01)
*A61K 39/00* (2006.01)

(52) U.S. Cl. ..... 424/234.1; 424/9.1; 424/9.2; 424/130.1; 424/163.1; 424/164.1; 424/184.1; 424/242.1; 435/243; 435/252.9

(58) Field of Classification Search .............. 424/9.1, 424/9.2, 130.1, 163.1, 164.1, 184.1, 243.1, 424/242.1, 234.1; 435/243, 252.9
See application file for complete search history.

(56) References Cited

U.S. PATENT DOCUMENTS

| | | | | |
|---|---|---|---|---|
| 3,794,732 | A | 2/1974 | Raun | 424/283 |
| 4,550,019 | A | 10/1985 | Polson | 424/85 |
| 5,367,054 | A | 11/1994 | Lee | 530/359 |
| 5,585,098 | A | 12/1996 | Coleman | 424/157.1 |
| 5,753,228 | A | 5/1998 | Sterling et al. | 424/581 |
| 7,238,351 | B2 | 7/2007 | Nash et al. | 424/130.1 |
| 2004/0043020 | A1* | 3/2004 | Nash et al. | 424/130.1 |

OTHER PUBLICATIONS

Avall-Jaakelainen, S., K. Kyla-Nikkila, M. Kahala, T. Miikkulainen-Lahti, and A. Palva, Surface Display of Foreign Epitopes on the *Lactobacillus brevis* S-Layer, Applied and Environmental Microbiology, vol. 68, No. 12, 5943-5951, 2002.
Bayrock, D and W.M. Ingledew, Changes in steady state on introduction of a *Lactobacillus* contaminant to a continuous culture ethanol fermentation, Journal of Industrial Microbiology & Biotechnology, 27, 39-45, 2001.
Chang, I.S., B.H. Kim, and P.K. Shin, Use of Sulfite and Hydrogen Peroxide to Control Bacterial Contamination in Ethanol Fermentation, Applied and Envirnomental Microbiology, vol. 63, No. 1, 1-6, 1997.
Chin, P.M. and W.M. Ingledew, Effect of lactic acid bacteria on wheat mash fermentations prepared with laboratory backset., Enzyme Microbiology Technology, vol. 16, 311-317, 1994.

De Oliva-Neto and F. Yokoya, Evaluation of bacterial contamination in a fed-batch alcoholic fermentation process, World Journal of Microbiology and Biotechnology, vol. 10, 697-699, 1994.
Hynes, S.H., D.M. Kjarsgaard, K.C. Thomas and W.M. Ingledew, Use of virginiamycin to control the growth of lactic acid bacteria during alcohol fermentation, Journal of Industrial Microbiology & Biotechnology, 18, 284-291, 1997.
Jespersen, L. and M. Jakobsen, Specific spoilage organisms in breweries and laboratory media for their detection, International Journal of Food Microbiology 33, 139-155, 1996.
Kleynmans, U. H.Heinzl, and W. P. Hammes, *Lactobacillus suebicus* sp. nov., An Obligately Heterofermentative *Lactobacillus* Species isolated from Fruit Mashes, System. Appl. Microbiology, 11, 267-271, 1989.
Larsson, A., Carlander, D., and Wilhelmsson, M., Antibody Response in Laying Hens with Small Amounts of Antigen, Food and Agricultural Immunology, 10, 29-36, 1998.
Leslie, Gerrie A., and Clem, L.W., Ph.D., Phylogeny of Immunoglobulin Structure and Function, Department of Microbiology, College of Medicine, University of Florida, Gainesville, Florida, 1337-1352, 1969.
Losch, U., Schranner, I., Wanke, R., and Jurgens, L., The Chicken Egg, an Antibody Source, J. Vet. Med. B, 33, 609-619, 1986.
Narendranath, N., S.H. Hynes, K.C. Thomas and W.M. Ingledew, Effects of Lactobacilli on Yeast-Catalyzed Ethanol Fermentations, Applied and Environmental Microbiology, vol. 63, No. 11, 4158-4163, 1997.
Narendranath, N., S.H. Hynes, K.C. Thomas and W.M. Ingledew, Ure Hydrogen Peroxide Reduces the Numbers of Lactobacilli, Nourishes Yeast and Leaves No Residues in the Ethanol Fermentation, Applied and Environmental Microbiology, vol. 66, No. 10, 4187-4192, 2000.
Narendranath, Naren, Infection Control Forum, Alcohol Times, pp. 1 and 3, Sep. 2003. Shinefield, H., M.D., Black, Steven, M.D., Fattom, A, Ph.D., Horwith, G., M.D., Rasgon, S., M.D., Ordonez, J., M.D., Yeoh, H., M.D., Law, D., M.D., Robbins, J.B., M.D., Schneerson, R., M.D., Muenz, L. Ph.D., and Naso, R., Ph.D., Use of a *Staphylococcus aureus* Conjugate Vaccine in Patients Receiving Hemodialysis, N. Engl. J. Med, vol. 346, No. 7, 491-496, 2002.
Simpson, W.J. and J. L. Fernandez, Selection of beer-spoilage lactic acid bacteria and induction of their ability to grow in beer, Letters in Applied Microbiology, 14, 13-16, 1992.
Thomas, K.C., S.H. Hynes and W.M. Ingledew, Effect of lactobacilli on yeast growth, viability and batch and semi-continuous alcohol fermentation of corn mash, Journal of Applied Microbiology, 90, 819-826, 2001.

(Continued)

*Primary Examiner* — Rodney P. Swartz
(74) *Attorney, Agent, or Firm* — Westman, Champlin & Kelly, P.A.; Z. Peter Sawicki; Visala Goswitz

(57) ABSTRACT

A microbial adherence inhibitor specific to lactic acid producing microorganisms, in the form of fowl egg antibodies is disclosed, along with the method of making it and methods of using it. The inhibitor functions by substantially preventing the attachment or adherence of colony-forming immunogens in the fermentators. The inhibitor is made by inoculating female birds with the immunogen, allowing time for an immune response in the female bird and then harvesting the eggs that contain antibodies to the immunogen. The egg contents can be dried or used as a liquid and added to the media in the fermentators. Dependent upon the particular immunogen with which the female bird is inoculated, the egg antibody will specifically bind to the specific immunogen. When bacteria such as *Lactobacillus* spp. infect fermentation systems, they will further reduce alcohol conversion efficiency. Colony forming immunogens such as *Lactobacillus* spp. (a major lactic acid producer) can be targeted by antibodies to enhance fermentation efficiency.

17 Claims, No Drawings

OTHER PUBLICATIONS

Whiting, M.S., S.L. Gares, W.M. Ingledew, and B. Ziola, Brewing spoilage lactobacilli detected using monoclonal antibodies to bacterial surface antigens, Can. J. Microbiology, 45, 51-58, 1999.

Whiting, M.S., W.M. Ingledew, S.Y. Lee, and B. Ziola, Bacterial surface antigen-specific monoclonal antibodies used ot detect beer spoilage Pediococci, Can.J. Microbiol., 45, 670-677, 1999.

Yasui, T., and Yoda, K., The Group E Antigen is Masked by the Paracrystalline Surface Layer in *Lactobacillus brevis*, Journal of Fermentation and Bioengineering, vol. 84, No. 1, 35-40, 1997.

Yasui, T., and Yoda, K., Imaging of *Lactobacillus brevis* Single Cells and Microcolonies without a Microscope by an Ultrasensitive Chemiluminescent Enzyme Immunoassay with a Photon-Counting Television Camera, Applied and Environmental Microbiology, vol. 63, No. 11, 4528-4533, 1997.

Yasui, T. and K. Yoda, Purification and partial characterization of an antigen specific *Lactobacillus brevis* strains with beer spoilage activity, FEMS Microbiology Letters, 151, 169-176, 1997.

Product Information Sheet for ATCC® 4356, 2003.
Product Information Sheet for ATCC® 9649, 2003.
Product Information Sheet for ATCC® 14917, 2003.
Product Information Sheet for ATCC® 7469, 2003.

* cited by examiner

IMMUNOGEN ADHERENCE INHIBITOR DIRECTED TO *LACTOBACILLUS* ORGANISMS AND METHOD OF MAKING AND USING IT

CROSS-REFERENCE TO RELATED APPLICATION

The present application is a continuation of and claims priority of U.S. patent application Ser. No. 11/784,868, filed Apr. 10, 2007, abandoned, the content of which is hereby incorporated by reference in its entirety.

FIELD OF THE INVENTION

This invention is directed to microbial adherence inhibitors in the form of fowl egg antibodies for substantially preventing the attachment or adherence of colony-forming immunogens or haptens of *Lactobacillus* spp. in fermentation processes such as fruit mashes, ethanol or beer production.

BACKGROUND OF THE INVENTION

The fuel ethanol fermentation is challenged by microbes that compromise yeast fermentation. Certain common bacterial immunogens of *Lactobacillus* and similar bacteria can contaminate fermentation flasks for things like alcohol production. These include but are not limited to *Lactobacillus* spp. Jespersen and Jakobsen, Int. J. Food Microbiology 33:139-155, 1996 review specific groups of gram positive bacteria that are generally considered hazardous beer spoilage organisms in modern breweries. This group of lactobacilli are considered the primary problem. Detection of specific organisms is not always easy with cultivation in laboratory media.

These microbes consume energy that would otherwise be available for the yeast and excrete materials that can inhibit the yeast fermentation. The *Lactobacillus* spp. often take a measurable toll on the productivity of fuel ethanol plants. For this reason, ethanol producers expend significant resources attempting to minimize these contaminates. Different strains of microbes can have different impacts on the type of fermentation. Hynes, et. al, J. Ind. Micro. and Biotech. 18:284-291, 1997 lists the following: *L. rhamnosus*, from corn steep liquor, *L. rhamnosus*, from fermented beets, *L. delbrueckii*, from sour grain mash, and *L. paracasei* and *L. plantarum*, from Brazilian industrial ethanol plant. Brewing, mashes, fermented foods may have problems with different strains from the ethanol plants. Hynes et al, tested the use of virginiamycin to control lactic acid bacteria using alcohol fermentation. They found that different strains of *Lactobacillus* had different levels of resistance to the antibiotic. It was clear using yeast and wheat mash that the level of virginiamycin would have to be monitored depending on the strain.

If there were a new product that could selectively kill or immobilize these problem species there would be a demand for the product. The bulk of ethanol production is currently manufactured via continuous fermentation, not batch and this continuous process requires constant management of contamination levels. It is likely that antibiotics are currently used for periodic adjustment of contamination levels in continuous processes. Newer plants tend to run with little to no antimicrobial additives. Clearly, there is a need to find newer ways to control these microbes in the fermentation process.

*Lactobacillus* spp. produce enzymes that contaminate fermentation processes. Bayrock and Ingledew, J. Ind. Microb. and Biotech. 27:39-45, 2001 report on the changes in steady state of a multistage continuous ethanol fermentation system when *Lactobacillus* of various species were added to a continuous culture for ethanol fermentation. They showed that different species of *Lactobacillus* were able to grow or be supported under the different conditions in the fermentor. They estimate that between 2% and 11% of ethanol yield is lost if the batch fermentation is contaminated with *Lactobacillus*. They did find that due to the unique media conditions, *L. paracasei* growth is supported only in the first fermentor stage of the multistage unit.

Chang, Kim and Shin, Applied and Environmental Microbiology, 63(1): 1-6, 1997 analyzed an industrial-scale ethanol fermentation process and isolated lactic acid bacteria from the process. They wanted to evaluate sulfite as a control agent in a cell-recycled continuous ethanol fermentation process. They found differences between the effect of sulfite on *L. casei* and *L. fermentum*. They conclude that sulfite could be used with no harm to the yeast to treat cell-recycled continuous ethanol fermentation processes.

Narendranath et. al., Applied and Environmental Microbiology, 63(11): 4158-4163, 1997 studied the effects of lactobacilli on yeast-catalyzed ethanol fermentation. They determined the production of lactic acid and the suspected competition with yeast cells were the major reasons for the reduction in yeast growth and final ethanol yield.

In many fermentation operations, the challenge is not the yeasts but relates to microbial growth rates and shifts in bacterial populations, and significantly influences the systemic metabolic state. De Oliva-Neto and Yokoya, World J. Microbiology and Biotechnology, 10: 697-699, 1994 evaluated the effect of bacterial contamination on a fed-batch alcoholic fermentation process. They showed that *L. fermentum* will strongly inhibit commercial baker's yeast in a batch-fed process. When the total acid exceeded 4.8 g/l it interfered with yeast bud formation and viability with 6 g/l decrease in alcoholic efficiency. They demonstrated the clear need for bacterial control in alcohol fermentation.

Simpson and Fernandez, Letters in Applied Microbiology, 14:13-16, 1992 demonstrated that there was a significant difference between lactic acid bacteria species and their resistance to hop-derived constituents of beer. Frequently, microorganisms isolated on growth media die when re-inoculated into beer. Beer-grown microorganisms tend to flourish when transferred from one beer to another. This becomes a major problem in the brewery industry for the microbiologist who is unable to separate the beer-spoilage lactic acid bacteria from the non-spoilage strains.

Jespersen and Jakobsen, Int. J. Food Microbiology, 33:139-155, 1996 review specific groups of gram positive bacteria that are generally considered hazardous to beer spoilage organisms in modern breweries. This group of *Lactobacillus* are considered the primary problem. Detection of specific organisms is not always easy with cultivation in laboratory media.

Thomas et. al., J. Applied Microbiology, 90:819-826, 2001 reported on the use of a large yeast inoculum in corn mashes to inhibit lactobacilli contamination during fermentation. This self regulating cascade system allowed for recovery of the yeast and had an insignificant effect on fermentation rate or ethanol yield. If however there were large numbers of the lactobacilli present in the incoming mash or in transfer lines, yeast growth and fermentation rates could be adversely affected. When lactobacilli was pre-cultured in the mash, yeast growth was inhibited and the production of ethanol was reduced by as much as 22%.

Chin and Ingeledew, Enzyme Microb. Technol. 16:311-317, 1994 studied the effect of lactic acid bacteria on wheat mash fermentation prepared with laboratory backset. Lactic acid bacteria are known to be most troublesome group of contaminating bacteria found in breweries, distilleries, and fuel alcohol plants. These bacteria are highly heat-resistant and can metabolize and multiply under low pH and anaerobic conditions. Backsetting is common in most fuel (25 to 75%) ethanol production plants. This can lead to a number of problems due to bacterial contaminants. This may lead to inhibition of ethanol production.

Kleynmans, et. al., System Appl. Microbiol., 11:267-271, 1989 isolated and identified a new strain of *Lactobacillus* from apple and pear mashes. The strain is called *L. suebicus*. The type strain is strain DSM. These fruit mashes can include fruit brandies and fruit mashes that are fermented and distilled.

A principal objective of the present invention is to substantially prevent the colonization of deleterious organisms such as *Lactobacillus* spp., as well as the growth of such organisms resulting in their substantial elimination from the system by the administration of fowl egg antibody to the specific organisms.

Haptens are partial or incomplete immunogens such as certain toxins, which cannot by themselves cause antibody formation but are capable of combining with specific antibodies. Such haptens may include bacterial toxin, yeast mold toxin, viruses, parasite toxins, algae toxins, etc.

Under the most popular fermentation systems, the problem with carry over and development of resistant strains of microorganisms are also of major concern to the industry. The use of broad-spectrum antibiotics has further drawbacks including vulnerability to human error, additional cost, consumer resistance, and the like. In addition, most antibiotic additives cannot be added with the commonly used media-based supplements. Avall-Jaskelainen et al., Applied and Environmental Microbiology, 68(12): 5943-5951, 2002 teaches that the *Lactobacillus brevis* has a number of S-layer epitopes that can be used to make antigens. They were able to construct model epitopes from *L. brevis* that were heterologous as part of the outermost proteinacous S-layer of the cell. It is proposed but not shown that they could immunize animals with these epitopes.

Narendranath et. al., Applied and Environmental Microbiology, 66(10): 4187-4192, 2000 were able to test the use of urea hydrogen peroxide in ethanol fermentation to control lactobacilli. They showed that it nourishes yeast and leaves no residues in the product. This was tested against five strains of *Lactobacillus* spp., i.e., *L. plantarum, L. paracasei*, L. sp. Strain 3, *L. rhamnosus* and *L. fermentum*. At a concentration of 32 mmol/liter it only serves as a disinfectant.

Narendranath, Alcohol Times, pages 1 and 3, September 2003 demonstrated from his research that some antimicrobials do not control *Lactobacillus* at all stages of the life cycle. Lactoside is a product designed to work at all stages as a broad spectrum control. It is currently the only product available. He developed a test for analyzing mash for contamination control. He estimates that 10 million or more cells of *Lactobacillus* per ml of mash is equivalent to a loss of alcohol yield of 1% or 400,000 gallons for 40 million gallons of alcohol. The main problem with these products are that resistance can occur. These infections rob the ethanol industry of millions of dollar each year.

PRIOR ART

The production of avian egg antibody for the diagnosis or treatment of specific conditions has been known. The production of avian egg antibody for the inhibition of organisms, specifically the colonization of organisms such as *Lactobacillus* spp. and the contamination of these immunogens is not suggested.

Representative prior art patents include the following:
Polson, U.S. Pat. No. 4,550,019
Lee, U.S. Pat. No. 5,367,054
Coleman, U.S. Pat. No. 5,585,098
Raun, U.S. Pat. No. 3,794,732, discusses the uses of polyester antibiotics in ruminant rations to improve the utilization of feed in ruminant animals. This specifically addresses the use of antibiotics in ruminant animals as growth promotants.

Poison, U.S. Pat. No. 4,550,019, is directed to the manufacture and use of fowl egg yolk antibodies for making immunological preparations for the passive immunizations of animals, including humans, as immuno reagents for immunosorbitive processes and in particular for quantitative analytical tests, especially micro assays for diagnostic, pathological, forensic, and pharmacokinetic investigations.

Lee, U.S. Pat. No. 5,367,054 is directed to methods for large-scale purification of egg immunoglobulin for the treatment of infections.

Coleman, U.S. Pat. No. 5,585,098 is directed to a method of oral administration of chicken yolk immunoglobulins to lower somatic cell count in the milk of lactating ruminants.

Yasui and Yoda, FEMS Microbiology Letters, 151:169-176, 1997 developed specific antigens for immunizing rabbits to develop specific antiserum to *Lactobacillus brevis* 578 strain. This antiserum was used to distinguish between Pediocuccus beer spoilers and non-spoilers in precipitation reactions.

Whiting et al., Can. J. Microbiology, 45:51-58, 1999 proposed the development of monoclonal antibodies to bacterial surface antigens of the brewing spoilage lactobacilli. They proposed that these reagents could be used to develop immunoassay technology for the detection of brewery contaminants. They could only develop a panel of 13 monoclonal antibodies that only bound to 8 of the 11 strains of *Lactobacillus* spp. They concluded that when using surface-reactive Mabs to detect *Lactobacillus* BSOs, it must be remembered that both brewery conditions and intrinsic bacterial factors can affect the stability of bacterial surface antigens involved in Mab binding.

Whiting et al., Can. J. Microbiol., 45:670-677, 1999 developed a series of fourteen monoclonal (Mabs) antibodies that react with surface antigens of *Pediococcus* beer spoilage organisms. They showed great potential for developing rapid immunoassay systems for detecting Pediocuccus beer spoilage organisms. These Mabs had to be assessed under actual brewing conditions to determine if they could be used to detect the correct surface antigens.

None of these references imply or teach that broad spectrum antibodies could be developed to control the microorganisms in the fermentor.

SUMMARY OF THE INVENTION

Broadly stated, this invention is directed to a method for the production of a microbial adherence inhibitor for administration to fermentation systems to substantially prevent the adherence of colony-forming immunogens or haptens to fermentors, which are not by themselves subject to target contamination, by first inoculating female birds, in or about to reach their egg laying age, with the particular target immunogen. Then, after a period of time sufficient to permit the production in the bird of antibody to the targeted immunogen, the eggs laid by the birds are harvested. The total antibody-containing contents of the eggs are separated from the shells and can be dried or used as a liquid. The egg contents may be dried on a carrier material or mixed with liquid extenders such as PBS or culture media. The dried or liquid separated egg adherence inhibiting material may be stored or shipped for use when needed.

The target immunogen with which the bird is inoculated depends upon the anticipated use of the inhibitor, a *Lactobacillus* spp. antibody where blocking contamination is the objective, and a targeted organism where the objective is the substantial reduction or elimination of contamination.

The egg contents incorporating the antibody specific to the targeted immunogen are administered to the fermentors by distributing the antibody material substantially uniformly throughout culture media and then supplying the resulting antibody-containing media to the fermentation method. When improved fermentation utilization is the objective, the antibody-containing media is supplied to the fermentors during the normal finishing stage. The substantial prevention of colonization of the targeted organism in the fermentor will ultimately permit substantial reduction or elimination of the organism from the system. This repression of colonization and elimination of the subject organism will permit a significant increase in fermentation efficiency. In addition, the resulting decrease in competition by the *Lactobacillus* spp. producing organism will further enhance the most efficient utilization of fermentation products.

The invention in one aspect comprises the production of an adherence inhibitor specific to *Lactobacillus* spp. and to the substantial reduction or elimination of lactic acid and contamination problems caused by these bacteria. Strains of *Lactobacillus* spp. include but are not limited to *L. plantarum, L. paracasei, L.* sp. Strain 3, *L. rhamnosus* and *L. fermentum, L. delbrueckii,* and *L. acidophilus*. The invention is described with particular reference to elimination of *Lactobacillus* spp. but it is understood that the invention is not so limited, but is equally applicable to elimination of contaminants caused by the other colony-forming immunogens and haptens in fermentation processes such as mashes, ethanol and beer production.

DESCRIPTION OF THE PREFERRED EMBODIMENTS

The present invention is based on the concept of specifically inhibiting the ability of colony-forming organisms such as *Lactobacillus* spp. to adhere to fermentors and thus reduces the ability of the organisms to multiply, grow, and colonize in fermentation systems. While the microbial inhibitors of the present invention may be administered at will by the producer, it is preferred for efficient fermentation that a carefully determined and regulated course of administration of the inhibitors during the finishing step at the fermentor be scheduled and followed. Such a predetermined level takes advantage of lower doses, longer cumulative effect and is easily integrated into current fermentation practices. This will provide the most economically attractive rate of return through improved non-contaminated fermentation products such as alcohol, beer, and other fermented foods or mashes.

For complete elimination of *Lactobacillus* organisms from end-products, the inhibitor may be administered either immediately at the beginning of fermentation or over some substantial period of the fermentation cycle. It is preferred that a carefully determined and managed mid-term period of administration at the fermentor level be followed.

Any organism that may contaminate the fermentor must possess the capability of sticking or adhering to that surface in order to multiply and grow. The specific organisms addressed by this invention are no exception to this rule. As other factors such as need of beneficial organisms for specific enzymes must also be considered, specific reagents are required to reduce the number of targeted organisms in the fermentor while not interfering with normal flora. The organism inhibitor of this invention strongly interferes with adherence in a highly specific manner and, on a cumulative basis, thereby prevents the targeted organisms from multiplying, growing, and colonizing. Through the vehicle of a simple daily addition, the product essentially supplies the fermentor with an antibody preparation designed not to kill the organisms but to dislodge any resident bacteria in the fermentor and to prevent attachment of any newly introduced numbers of that same bacteria. The microbial inhibitor has no direct effect whatsoever on the ultimate food products or end-products and leaves absolutely no undesirable residue in the fermentor or in the ultimate fermented products. In addition, since the deleterious organisms are prevented from multiplying, they, over time (for example, the 72 hr fermentation period), can be filtered out of the media, helping to eliminate that significant potential source of recontamination. The inhibitor product itself can be classified as a natural material of animal origin and as such can be used in almost any kind of fermentation program. As the active ingredients are completely natural, they will work well with most media additives, including serum-based media supplements.

All mammals and birds provide similar types of protection, which allow for an immediate immune response in their very young offspring until they too acquire the ability to make the antibodies for themselves. More specifically called passive antibody protection, this defense mechanism is passed to the young of mammals through the placenta, the mother's milk, or through both. The young of birds, however, receive their passive antibody protection through the store of antibodies in the eggs in which they develop from the embryonic stage. Birds, in particular, have the ability to "load up" their eggs as they are formed with a very large supply of antibodies concentrated many fold over which is present in the serum of the mother. In addition, avian antibodies are much more stable and resistant than mammalian antibodies from rabbits or mice, especially under adverse conditions (Sterling, U.S. Pat. No. 5,753,268). Once immunized, the hen layers the unique IgY types immunoglobulins in the yolk while depositing the common chicken IgM and IgA immunoglobulins in the albumin. The albumin helps give the heat resistance to the whole egg preparations and helps protect the avian antibodies. Furthermore, the large quantities of antibodies, which are placed in eggs, are much more exclusively those specific for the antigens to which the mother has most recently been exposed to and challenged by. This all results in the eggs of birds being the most ideal source for large quantities of economically produced, highly specific and stable antibodies. While the invention is illustrated by the use of chickens to produce avian antibody, other fowl including turkeys, ducks, geese, etc. may be used. Specifically, groups are obtained of young hen chickens (typically Rhode Island Red, White Leghorns, hybrid crosses, or other breeds suited to large egg size or greater and to high volume egg production) which are about to reach egg laying age, about 19 weeks for chickens, on a schedule predetermined by the amount and timing of final product desired resulting in a steady continuous production stream. After a suitable period of isolation and acclimatization of about 2 to 4 weeks, each group will enter into an inoculation program using proprietary preparation of specific antigens to which an antibody is desired. The antigens may be obtained from commercial sources such as the American Type Culture Collection (ATCC). The antigen may be injected intramuscularly, but preferably injected sub-cutaneously. In approximately four weeks, the average egg collected will contain copious amounts of the desired specific antibody in a readily usable and stable form. The chickens may be reinoculated with the targeted antigen throughout the egg laying period to maintain the high antibody level.

Batches of eggs from predetermined groups of chickens are cracked, the liquid egg contents are separated from the shells and mixed and preferably pasteurized (to eliminate potential pathogenic microorganism from the chicken and thus reduce potential contamination of media). The total egg content is dried using standard commercial methods, such as spray drying using ambient or hot air up to 50° C. and tested to determine overall titer or antibody level. The egg contents may be used as a liquid, dried alone or on extenders such as dry soy or rice husks or the like. Standard test procedures are used, such as ELISA, or agglutination, or the like to detect the antibody. The typical batch is then blended with batches from other groups of chickens at other average production levels resulting in a lot of standardized active ingredient. The dried egg antibody microbial inhibitor material may be stored and shipped on carrier materials such as soybean hulls, pellets and/or tablets. Dependent on the needs and specifications of the feed formulator and the final customer, the final antibody product may include some type of innocuous additive, such as dried whey or dried soy protein powder, dried soy or rice husks, or the like for formulation with the culture ration. One egg produced and processed by the above procedures will yield a product sufficiently active and stable to provide many daily doses of managed protection against microbial colonization. This method provides for the first time, an economical, safe, and effective means for controlling fermentation efficiency organisms in fermentors, and an economical, safe and effective means for controlling *Lactobacillus* spp. and other contaminant in culture media.

The present invention specifically addresses fermentation efficiency as it relates to fermentors such as for alcohol, beer, etc, and to the problem of eliminating contaminating organisms from fermentation systems. However, the concept of preventing microbial adherence has great economic potential for a number of diverse food safety and production applications. One such field of application is in alcohol production and water targeting specific undesirable microorganisms. An example of this application would include products to actively inhibit even spoilage microorganisms in beer production. Another such field of application is as rinse aid ingredients targeted to specific undesirable microorganisms. Examples of this application include products to actively dislodge pathogenic or even spoilage microorganisms for use in solutions for spot cleaning and rinsing beef carcasses or for chilling poultry after they have been dressed.

The most successfully colonizing microorganisms, bacteria, viruses, and parasites, etc., have evolved a number of different types of molecules, referred to as "adherins," on their surfaces which can very tightly stick to one or more molecules that are part of the host's various surfaces. The adhesion inhibitor is an avian antibody of extraordinarily high specific activity which can very tightly bind to coat, cover, and obliterate these "adherins" which attach themselves to their hosts with a lock and key type of fit to very unique chemical structures. In addition to this direct attack, components of the complement system included in most biological fluids, such as blood, lymph, saliva, tears, and to some extent, intestinal secretions, recognize an antibody attachment as triggers for their many types of defensive activities. Specific antibody attachment and coating combined with the very likely mobilization of many other cellular defense systems, therefore quickly culminates inactivation and ultimately the destruction of the targeted microorganism.

The invention is further illustrated by the following examples:

Example 1

Selection of Egg Laying Avian Hens

The strain of egg laying hens may vary with needs and uses. Any egg laying fowl hens may be immunized including chickens, turkeys, ducks, emus, or any other fowl. The common strains of egg laying chickens are the preferred and are usually selected for the number of eggs laid per year, size of egg, and ease of housing. Rhode Island Red, White Leghorn, and Red Sex Linked hybrids are the animals of choice based on egg size (large to ex-large, 50-65 gm) and were used for the immunization schedules. The ease of handling the animals and the size and uniformity of the eggs along with the number of eggs laid per hen per year were observed. Although any avian egg-laying hen could be used, for cost and ease of use, these chickens proved to work the best. The Red Sex Linked hybrid gave the most uniformity and greater number of eggs per animal. These animals produce a large to extra-large grade of egg (50-65 gm) and up to 300 eggs a year per hen.

Example 2

Preparation of Stock Culture

The American Type Culture Collection *Lactobacillus delbrueckii*, Stock ATCC 9649 was used as the first model bacterium. The organism was isolated from sour grain mash fermentation. The ATCC method for rehydration of the stock was followed. The bacterium is rehydrated in 1.0 ml of MRS Broth (Lactobacilli MRS Broth, Difco 288130), transferred to 5 ml of MRS sterile broth, and incubated overnight (approx. 18 hrs) at 37° C. Nice turbid growth was observed. This was used as stock as needed. It was streaked on MRS Agar (Difco) for verification of colony production.

Example 3

Preparation of Stock Culture

The American Type Culture Collection *Lactobacillus plantarum, Stock ATCC* 14917 was used as the second model bacterium. The organism was isolated from pickled cabbage. The ATCC method for rehydration of the stock was followed. The bacterium is rehydrated in 1.0 ml of MRS Broth (Lactobacilli MRS Broth, Difco 288130), transferred to 5 ml of MRS sterile broth, and incubated overnight (approx. 18 hrs) at 37° C. Nice turbid growth was observed. This was used as stock as needed. It was streaked on MRS Agar (Difco) for verification of colony production.

Example 4

Preparation of Stock Culture

The American Type Culture Collection *Lactobacillus rhamnosus*, Stock ATCC 7469 was used as the second model bacterium. The organism was isolated from fermented casein. The ATCC method for rehydration of the stock was followed. The bacterium is rehydrated in 1.0 ml of MRS Broth (Lactobacilli MRS Broth, Difco 288130), transferred to 5 ml of MRS sterile broth, and incubated overnight (approx. 18 hrs)

at 37° C. Nice turbid growth was observed. This was used as stock as needed. It was streaked on MRS Agar (Difco) for verification of colony production.

Example 5

Preparation of Stock Culture

The American Type Culture Collection *Lactobacillus acidophilus*, Stock ATCC 4356 was used as the second model bacterium. The organism was isolated from a human. The ATCC method for rehydration of the stock was followed. "Product Information Sheet for ATCC© 4356, ATCC©, 2003". The bacterium is rehydrated in 1.0 ml of MRS Broth (Lactobacilli MRS Broth, Difco 288130), transferred to 5 ml of MRS sterile broth, and incubated overnight (approx. 18 hrs) at 37° C. and 5% $CO_2$. Nice turbid growth was observed. This was used as stock as needed. It was streaked on MRS Agar (Difco) for verification of colony production.

Example 6

Preparation of LD Antigen for "LD" Immunogen

The MRS was used for "LD" Antigen Production. It is a standard medium for stimulating adherence antigens for *L. delbrueckii*. These cultures must be grown under aerobic conditions. The stock culture was grown according to ATCC direction. "Product Information Sheet for ATCC© 9649, ATCC©, 2003". Subcultures are grown in small amounts. Flasks of MRS are inoculated with subculture of *L. delbrueckii*. Flasks were incubated at 35° C. for 48-72 hours depending on apparent growth. Flasks were combined and the product was harvested using centrifugation at approximately 2500 rpm for 30 minutes, collected in tubes, and run at low speed for 30 minutes. Density was checked. The mixture was heated at 60° C. for 40 minutes (as needed) to inactivate. In some cases, 0.8% formaldehyde was added to make stock immunogen. Mixture was centrifuged to remove whole cells. Dry weight was determined (approximately 20.5 mg/ml). The product was diluted with PBS, pH 7.4, to 1 mg/ml for "LD" Immunogen. Thioglycollate Media (Difco) was inoculated with the stock and incubated for 48 hours.

Example 7

Preparation of LP Antigen for "LP" Immunogen

The MRS was used for "LP" Antigen production. It is the standard medium for stimulating adherence antigens for *L. plantarum*. The stock culture was grown according to ATCC direction. Product Information Sheet for ATCC© 14917, ATCC©, 2003. Subcultures were grown in small amounts. Flasks (MRS) were inoculated with subculture of *L. plantarum*. Flasks were incubated at 37° C. for 48-72 hours depending on apparent growth. Flasks were combined and the product was harvested using centrifugation at approximately 2500 rpm for 30 minutes, collected in tubes, and run at low speed for 30 minutes. Density was checked. The mixture was heated at 60° C. for 40 minutes (as needed) to inactivate. In some cases, 0.8% formaldehyde was added to make stock immunogen. Mixture was centrifuged to remove whole cells. Dry weight was determined (approximately 20.5 mg/ml). The product was diluted with PBS, pH 7.4, to 1 mg/ml for "LP" immunogen. Thighlycollate Media (Difco) was inoculated with the stock and incubated for 48 hours.

Example 8

Preparation of LR Antigen for "LR" Immunogen

The MRS was used for "LR" Antigen production. It is the standard medium for stimulating adherence antigens for *L. rhamnosus*. The stock culture was grown according to ATCC direction. Product Information Sheet for ATCC© 7469, ATCC©, 2003. Subcultures were grown in small amounts. Flasks (MRS) were inoculated with subculture of *L. rhamnosus*. Flasks were incubated at 37° C. for 48-72 hours depending on apparent growth. Flasks were combined and the product was harvested using centrifugation at approximately 2500 rpm for 30 minutes, collected in tubes, and run at low speed for 30 minutes. Density was checked. The mixture was heated at 60° C. for 40 minutes (as needed) to inactivate. In some cases, 0.8% formaldehyde was added to make stock immunogen. Mixture was centrifuged to remove whole cells. Dry weight was determined (approximately 20.5 mg/ml). The product was diluted with PBS, pH 7.4, to 1 mg/ml for "LR" immunogen. Thighlycollate Media (Difco) was inoculated with the stock and incubated for 48 hours.

Example 9

Preparation of LA Antigen for "LA" Immunogen

The MRS was used for "LA" Antigen production. It is the standard medium for stimulation adherence antigens for *L. acidophilus*. The stock culture was grown according to ATCC direction. Product Information Sheet for ATCC© 4356, ATCC©, 2003. Subcultures were grown in small amounts. Flasks (MRS) were inoculated with subculture of *L. acidophilus*. Flasks were incubated at 37° C. for 48-72 hours depending on apparent growth. Flasks were combined and the product was harvested using centrifugation at approximately 2500 rpm for 30 minutes, collected in tubes, and run at low speed for 30 minutes. Density was checked. The mixture was heated at 60° C. for 40 minutes (as needed) to inactivate. In some cases, 0.8% formaldehyde was added to make stock immunogen. Mixture was centrifuged to remove whole cells. Dry weight was determined (approximately 20.5 mg/ml). The product was diluted with PBS, pH 7.4, to 1 mg/ml for "LP" immunogen. Thighlycollate Media (Difco) was inoculated with the stock and incubated for 48 hours.

Culturing was done in an isolation hood with use of a conventional incubator. Sterility was tested by inoculating thioglycollate tubes with each immunogen prep and incubated at 37° C. for 2-7 days.

Example 10

Preparation of ELISA Plates Using LD Antigens for Monitoring Antibodies in Eggs "LD" ELISA's ninety-six well assay plates (flat bottom Costar) were coated using 100 µl/well with various concentrations of antigens (LD) combination: 10 mg-100 µg/ml in carbonate buffer, pH 9.6. Plates were incubated between 22-37° C. for up to 18 hours. The wells were aspirated to prevent cross-contamination. The plates were blocked with 380 µl/well of 0.05% BSA and incubated at 37° C. for 1 hour. Plates were coated using alternate rows for positive or negative for controls. Plates were rinsed 1× with washer buffer containing Tween™ 20.

To run a test: One hundred microliters per well of diluted egg sample were added to wells in duplicate wells, and incubated at 37° C. for one hour. Goat anti-chicken IgG conjugate with Horseradish peroxidase (Kirkegard and Perry Laboratories; 1:1000-1:3000) was added. After 1-hour incubation, the substrate (3',3',5',5-tetramethylbenzidine (TMB), KPL, Inc. of Gaithersburg, Md. (KPL) was added according to manufacturer's instructions and the reaction was stopped after 10 minutes with 0.1 M phosphoric acid. Optical densities of the wells are determined in Dynatech ELISA Reader at 450 nm and the information was recorded for further data analysis.

Example 11

Preparation of ELISA Plates Using LP Antigens for Monitoring Antibodies in Eggs

"LP" ELISA's ninety-six well assay plates (flat bottom Costar) were coated using 100 µl/well with various concentrations of antigens (LP) combination: 10 mg-100 µg/ml in carbonate buffer, pH 9.6. Plates were incubated between 22-37° C. for up to 18 hours. The wells were aspirated to prevent cross-contamination. The plates were blocked with 380 µl/well of 0.05% BSA and incubated at 37° C. for 1 hour. Plates were coated using alternate rows for positive or negative for controls. Plates were rinsed 1× with washer buffer containing Tween™ 20.

To run a test: One hundred microliters per well of diluted sample were added to wells in duplicate wells, and incubated at 37° C. for one hour. Goat anti-chicken IgG conjugate with Horseradish peroxidase (Kirkegard and Perry Laboratories; 1:1000-1:3000) was added. After 1-hour incubation, the substrate (TMB from KPL) was added according to manufacturer's instructions and the reaction was stopped after 10 minutes with 0.1 M phosphoric acid. Optical densities of the wells are determined in Dynatech ELISA Reader at 450 nm and the information was recorded for further data analysis.

Example 12

Preparation of ELISA Plates Using LR Antigens for Monitoring Antibodies in Eggs

"LR" ELISA's ninety-six well assay plates (flat bottom Costar) were coated using 100 µl/well with various concentrations of antigens (LR) combination: 10 mg-100 µg/ml in carbonate buffer, pH 9.6. Plates were incubated between 22-37° C. for up to 18 hours. The wells were aspirated to prevent cross-contamination. The plates were blocked with 380 µl/well of 0.05% BSA and incubated at 37° C. for 1 hour. Plates were coated using alternate rows for positive or negative for controls. Plates were rinsed 1× with washer buffer containing Tween™ 20.

To run a test: One hundred microliters per well of diluted sample were added to wells in duplicate wells, and incubated at 37° C. for one hour. Goat anti-chicken IgG conjugate with Horseradish peroxidase (Kirkegard and Perry Laboratories; 1:1000-1:3000) was added. After 1-hour incubation, the substrate (TMB from KPL) was added according to manufacturer's instructions and the reaction was stopped after 10 minutes with 0.1 M phosphoric acid. Optical densities of the wells are determined in Dynatech ELISA Reader at 450 nm and the information was recorded for further data analysis.

Example 13

Preparation of ELISA Plates Using LA Antigens for Monitoring Antibodies in Eggs

"LA" ELISA's ninety-six well assay plates (flat bottom Costar) were coated using 100 µl/well with various concentrations of antigens (LA) combination: 10 mg-100 µg/ml in carbonate buffer, pH 9.6. Plates were incubated between 22-37° C. for up to 18 hours. The wells were aspirated to prevent cross-contamination. The plates were blocked with 380 µl/well of 0.05% BSA and incubated at 37° C. for 1 hour. Plates were coated using alternate rows for positive or negative for controls. Plates were rinsed 1× with washer buffer containing Tween™ 20.

To run a test: One hundred microliters per well of diluted sample were added to wells in duplicate wells, and incubated at 37° C. for one hour. Goat anti-chicken IgG conjugate with Horseradish peroxidase (Kirkegard and Perry Laboratories; 1:1000-1:3000) was added. After 1-hour incubation, the substrate (TMB from KPL) was added according to manufacturer's instructions and the reaction was stopped after 10 minutes with 0.1 M phosphoric acid. Optical densities of the wells are determined in Dynatech ELISA Reader at 450 nm and the information was recorded for further data analysis.

Example 14

Immunization of Chicken with LD Immunogen

Selected egg laying hens (White Leghorn Hy-Line W98), approximately 16-19 weeks old, are injected with the stock "LD" Immunogen. Four injections (500 µg, 100 µg, 250 µg, and 50 µg) are given 1 week apart. Serum samples are collected two weeks after the last initial injection. If boosters were needed, 100 µg was given in each booster (every 6 months). Within 4 weeks, hens produced excellent antibodies in the eggs.

Example 15

Immunization of Chicken with LP Immunogen

Selected egg laying hens (White Leghorn Hy-Line W98), approximately 16-19 weeks old, are injected with the stock "LP" Immunogen. Four injections (500 µg, 100 µg, 250 µg, and 50 µg) are given 1 week apart Serum samples are collected two weeks after the last initial injection. If boosters were needed, 100 µg was given in each booster (every 6 months). Within 4 weeks, hens produced excellent antibodies in the eggs.

Example 16

Immunization of Chicken with LR Immunogen

Selected egg laying hens (White Leghorn Hy-Line W98), approximately 16-19 weeks old, were injected with the stock "LR" Immunogen. Four injections (500 µg, 100 µg, 250 µg, and 50 µg) were given 1 week apart. Serum samples were collected two weeks after the last initial injection. If boosters were needed, 100 µg was given in each booster (every 6 months). Within 4 weeks, hens produced excellent antibodies in the eggs.

Example 17

Immunization of Chicken with LA Immunogen

Selected egg laying hens (White Leghorn Hy-Line W98), approximately 16-19 weeks old, were injected with the stock "LA" Immunogen. Four injections (500 µg, 100 µg, 250 µg, and 50 µg) were given 1 week apart. Serum samples were collected two weeks after the last initial injection. If boosters were needed, 100 μg was given in each booster (every 6 months). Within 4 weeks, hens produced excellent antibodies in the eggs.

Example 18

Process for Preparation of Whole Egg Material

Specific commercial strains of Hy-Line W98 egg laying hens were immunized with specific immunogen. Eggs were collected from hens on a daily basis. They were washed with soap and water, and then dripped in 0.05% bleach. The shells were air-dried.

Example 19

Analysis of Production Eggs Over Time: "LD"

During the product development phase, samples of the whole egg preparations were analyzed using the ELISA systems for "LD" Immunogen to monitor activity over time after the initial immunization schedule was completed. Selected animals from each group were placed into the production group. The average ELISA OD readings for the fourth through the sixth months are given in the table below. The eggs were sampled using 250μ of the whole egg and diluted 1:500 and 1:2,500 in PBS buffer and then run in the appropriate ELISA to determine the average OD reading at each dilution. The negative control readings were subtracted from each reading. The injected Immunogens stimulated different responses in the animals along with good specificity.

Example 20

Preparation of Stock Production Whole Egg Reagents

Random groups of selected eggs were combined from the Immunogen groups for the lactobacilli, to be used to produce production batches of whole egg reagents. The eggs were randomized and shells removed. The whole egg was mixed well and pasteurized using standard conditions (60° C., 140° F.) for 3.5 min (Charley, H. and C. Weaver, $3^{rd}$ edition, Food: a scientific approach, Merrill-Prentice Hall, P. 350, 1998). Temperature was recorded with a Fisher traceable scientific thermometer. Once pasteurized, samples were tested for activity and stored at 4° C. until dried or sprayed onto carriers. Samples of 250 μl were analyzed. Examples of results for ELISAs are given. Negative controls are subtracted to get final optical density (OD) reading.

| Pasteurized Whole Egg: | |
| --- | --- |
| Sample | Lactobacillus delbrueckii |
| PG-252 | 1.54 OD S/N 7.00 (signal of noise ratio) |
| PG-252 | 0.70 OD S/N 4.95 |
| PG-249 | 1.53 OD S/N 4.10 |
| PG-249 | 0.89 OD S/N 4.85 |

| Pasteurized Whole Egg: | |
| --- | --- |
| Sample | Lactobacillus plantarum |
| PG-252 | 1.79 OD S/N 7.69 |
| PG-252 | 0.82 OD S/N 5.25 |
| PG-249 | 1.76 OD S/N 5.13 |
| PG-249 | 1.16 OD S/N 9.59 |

| Pasteurized Whole Egg: | |
| --- | --- |
| Sample | Lactobacillus rhamnosus |
| PG-252 | 0.74 OD S/N 2.96 |
| PG-252 | 0.21 OD S/N 2.51 |
| PG-249 | 0.81 OD S/N 2.57 |
| PG-249 | 0.25 OD S/N 1.87 |

| Pasteurized Whole Egg: | |
| --- | --- |
| Sample | Lactobacillus acidophilus |
| PG-252 | 1.23 OD S/N 4.88 |
| PG-252 | 0.56 OD S/N 3.36 |
| PG-249 | 0.97 OD S/N 2.91 |
| PG-249 | 0.61 OD S/N 4.43 |

Example 21

Fresh Eggs Vs Freeze Dried Materials

Although whole eggs can be dispensed in water and used directly in fermentation media, the product may have to be dried to make it convenient to the users. In this study, fresh eggs were used to make freeze dried material. The material was then tested against similar fresh eggs using the ELISA coated plated.

| Antigen | Lactobacillus Immunogen |
| --- | --- |
| LR-Fresh egg | 1.08 OD S/N 4.05 |
| LP-Fresh egg | 2.35 OD S/N 7.86 |
| LA-Fresh egg | 1.26 OD S/N 5.61 |
| LD-Fresh egg | 2.71 OD S/N 8.62 |
| LR-Freeze Dried | 1.60 OD S/N 4.47 |
| LP-Freeze Dried | 2.44 OD S/N 7.47 |
| LA-Freeze Dried | 1.41 OD S/N 4.55 |
| LD-Freeze Dried | 2.77 OD S/N 7.97 |

Example 22

Analysis of Eggs for Antibody Activity: "LR" Product

Samples of the eggs were analyzed using the ELISA systems for "LR" Immunogens to monitor activity. Good antibody response was recorded after the processing of the Production Whole Egg batches. One-gram samples of the eggs were extracted and analyzed. Data for four batches taken is given in the table below (Average OD-Negative Control and Signal to Noise ratio (S/N)):

| Batches: | LR Immunogen |
| --- | --- |
| PG-253-7/10 | 1.50 OD S/N 1.83 |
| PG-248-7/6 | 1.70 OD S/N 3.83 |
| PG-249-7/10 | 1.94 OD S/N 5.27 |

Example 23

Analysis of Eggs for Antibody Activity: "LP" Product

Samples of the eggs were analyzed using the ELISA systems for "LP" Immunogens to monitor activity. Good antibody response was recorded after the processing of the Production Whole Egg batches. One-gram samples of the eggs were extracted and analyzed. Data for four batches taken is given in the table below (Average OD-Negative Control and Signal to Noise ratio (S/N)):

| Batches: | LP Immunogen |
| --- | --- |
| PG-253-7/10 | 1.15 OD S/N 2.14 |
| PG-248-7/6 | 2.35 OD S/N 2.50 |
| PG-250-7/10 | 1.65 OD S/N 1.86 |
| PG-249-7/5 | 1.60 OD S/N 4.25 |

Example 24

Analysis of Eggs for Antibody Activity: "LA" Product

Samples of the eggs were analyzed using the ELISA systems for "LA" Immunogens to monitor activity. Good antibody response was recorded after the processing of the Production Whole Egg batches. One-gram samples of the eggs were extracted and analyzed. Data for four batches taken is given in the table below (Average OD-Negative Control and Signal to Noise ratio (S/N)):

| Batches: | LA Immunogen |
| --- | --- |
| PG-253-7/10 | 0.95 OD S/N 1.94 |
| PG-248-7/6 | 2.24 OD S/N 3.12 |
| PG-250-7/10 | 1.43 OD S/N 5.06 |
| PG-249-7/5 | 1.40 OD S/N 3.44 |

Example 25

Analysis of Eggs for Antibody Activity: "LD" Product

Samples of the eggs were analyzed using the ELISA systems for "LD" Immunogens to monitor activity. Good antibody response was recorded after the processing of the Production Whole Egg batches. One-gram samples of the eggs were extracted and analyzed. Data for four batches taken is given in the table below (Average OD-Negative Control and Signal to Noise ratio (S/N)):

| Batches: | LD Immunogen |
| --- | --- |
| PG-253-7/10 | 1.15 OD S/N 2.27 |
| PG-248-7/6 | 2.21 OD S/N 3.17 |
| PG-250-7/10 | 1.43 OD S/N 5.20 |
| PG-249-7/5 | 1.42 OD S/N 3.85 |

Any microorganisms which contaminate the fermentor for mashes, ethanol or beer production must possess the capability of sticking or adhering to that surface in order to multiply. Organisms that promote the production of harmful accumulations of lactic acid in the fermentor and *Lactobacillus* spp. are no exception. The adherence inhibitors of this invention strongly interfere with the adherence and, on a cumulative basis, thereby prevent the specific targeted microorganism from colonizing and multiplying. Through the vehicle of a simple daily fermentor additive, the product essentially supplies the producer with a specific antibody preparation designed not to kill any microorganisms but to dislodge any resident bacteria and to prevent the attachment of any newly introduced bacteria in the fermentor. The adherence inhibitor has no direct effect on the end-product itself, leaves no undesirable residue in the fermentor and thus has no effect whatsoever on the ultimate products such as ethanol, beer or fruit mashes.

Although the present invention has been described with reference to preferred embodiments, workers skilled in the art will recognize that changes may be made in form and detail without departing from the spirit and scope of the invention.

The invention claimed is:

1. A method of controlling the incidence of *Lactobacillus* spp. in fermentors, which method comprises:
administering to fermentors a microbial adherence inhibitor wherein the inhibitor controls the incidence of lactic acid producing immunogen in fermentors by preventing or reducing the adherence of colony forming lactic acid producing immunogens, wherein the prevention or reduction of adherence is generated by applying the contents of eggs comprising the microbial adherence inhibitor, the eggs laid by female birds inoculated with a lactic acid producing immunogen cultured to stimulate adherence antigens.

2. The method of claim 1 wherein:
said lactic acid producing immunogen comprises *Lactobacillus* spp.

3. The method of claim 2 wherein *Lactobacillus* spp. comprises *L. delbrueckii, L. acidophilus, L. plantarum, L. rhamnosus* or *L. fermentom*.

4. The method of claim 1 including:
separating the contents of the eggs from the egg shells; and
drying the separated antibody-containing contents of said eggs.

5. The method of claim 4 wherein:
said lactic acid producing immunogen comprises *Lactobacillus* spp.

6. The method of claim 5 wherein *Lactobacillus* spp. comprises *L. delbrueckii, L. acidophilus, L. plantarum, L. rhamnosus* or *L. fermentom*.

7. The method of claim 1 wherein:
said colony forming lactic acid producing immunogen is from the genus consisting of *Lactobacillus* spp.

8. A microbial adherence inhibitor comprising an antibody in the contents of an egg or eggs, wherein the egg or eggs are laid by female birds inoculated with a lactic acid producing immunogen cultured to stimulate adherence antigens wherein administration of the microbial adherence inhibitor to fermentors controls the incidence of lactic acid producing immunogen in fermentors by preventing or reducing the adherence of colony forming lactic acid producing immunogens, wherein the inhibitor is in liquid form achieved by using separated antibody-containing contents of said eggs.

9. A microbial adherence inhibitor comprising
an antibody in the contents of eggs laid by female birds inoculated with LA antigen from *Lactobacillus acidophilus* cultured to stimulate adherence antigens, wherein administration of the microbial adherence inhibitor to fermentors controls the incidence of *Lactobacillus acidophilus* in fermentors by preventing or reducing the adherence of *Lactobacillus acidophilus*.

10. A microbial adherence inhibitor comprising
an antibody in the contents of eggs laid by female birds inoculated with LR antigen from *Lactobacillus rhamnosus* cultured to stimulate adherence antigens, wherein administration of the microbial adherence inhibitor to fermentors controls the incidence of *Lactobacillus rhamnosus* in fermentors by preventing or reducing the adherence of *Lactobacillus rhamnosus*.

11. A method for reducing or eliminating the incidence of lactic acid in fermentors, said method comprising:
administering to fermentors a microbial adherence inhibitor wherein the inhibitor reduces the levels of lactic acid in the fermentor by controlling the incidence of lactic acid producing immunogen by preventing or reducing the adherence of colony forming lactic acid producing immunogens, wherein the prevention or reduction of adherence is generated by applying the contents of an egg or eggs comprising the microbial adherence inhibitor produced in eggs laid by female birds inoculated with a lactic acid producing immunogen cultured to stimulate adherence antigens.

12. The method of claim 11 wherein:
said lactic acid forming immunogens are selected from the genus consisting of *Lactobacillus* spp.

13. The method of claim 1 further comprising:
allowing a period of time sufficient to permit the production in the birds of antibody to the lactic acid producing immunogen;
harvesting the eggs laid by the birds; and
separating the antibody-containing contents of said eggs from the shells to obtain the microbial adherence inhibitor.

14. A microbial adherence inhibitor comprising
an antibody in the contents of an egg or eggs, wherein the egg or eggs are laid by female birds inoculated with a lactic acid producing immunogen cultured to stimulate adherence antigens wherein administration of the microbial adherence inhibitor to fermentors controls the incidence of lactic acid producing immunogen in fermentors by preventing or reducing the adherence of colony forming lactic acid producing immunogens, wherein the female birds after inoculation are allowed a period of time sufficient to permit the production in the birds of antibody to the lactic acid producing immunogen, the eggs laid by the birds are harvested and the antibody-containing contents of the eggs are separated from the shells and dried.

15. The microbial adherence inhibitor of claim 9 wherein the female birds after inoculation are allowed a period of time sufficient to permit the production in the birds of antibody to the lactic acid producing immunogen, the eggs laid by the birds are harvested and the antibody-containing contents of the eggs are separated from the shells and dried.

16. The microbial adherence inhibitor of claim 10 wherein the female birds after inoculation are allowed a period of time sufficient to permit the production in the birds of antibody to the lactic acid producing immunogen, the eggs laid by the birds are harvested and the antibody-containing contents of the eggs are separated from the shells and dried.

17. The method according to claim 11 further comprising:
allowing a period of time sufficient to permit the production in the birds of antibody to the lactic acid producing immunogen;
harvesting the eggs laid by the birds; and
separating the antibody-containing contents of said eggs from the shells to obtain the microbial adherence inhibitor.

* * * * *